US010603172B2

(12) United States Patent
Faccioli et al.

(10) Patent No.: US 10,603,172 B2
(45) Date of Patent: Mar. 31, 2020

(54) ABSORBING ELUTING SPACER DEVICE

(71) Applicant: TECRES S.p.A., Sommacampagna (Verona) (IT)

(72) Inventors: Giovanni Faccioli, Monzambano (IT); Renzo Soffiatti, Nogara (IT)

(73) Assignee: TECRES S.P.A., Sommacampagna (VR) (IT)

( * ) Notice: Subject to any disclaimer, the term of this patent is extended or adjusted under 35 U.S.C. 154(b) by 57 days.

(21) Appl. No.: 15/523,811

(22) PCT Filed: Oct. 30, 2015

(86) PCT No.: PCT/IB2015/058416
§ 371 (c)(1),
(2) Date: May 2, 2017

(87) PCT Pub. No.: WO2016/071816
PCT Pub. Date: May 12, 2016

(65) Prior Publication Data
US 2017/0319345 A1    Nov. 9, 2017

(30) Foreign Application Priority Data
Nov. 6, 2014    (IT) .............................. VR2014A0274

(51) Int. Cl.
*A61F 2/30* (2006.01)
*A61B 17/56* (2006.01)
(52) U.S. Cl.
CPC ............ *A61F 2/30* (2013.01); *A61F 2/30724* (2013.01); *A61B 2017/561* (2013.01);
(Continued)

(58) Field of Classification Search
CPC ............ A61F 2002/30672; A61F 2002/30677
See application file for complete search history.

(56) References Cited

U.S. PATENT DOCUMENTS 5,522,895 A * 6/1996 Mikos ...................... A61F 2/28
606/76
2005/0169893 A1    8/2005 Koblish et al.
(Continued)

FOREIGN PATENT DOCUMENTS

| GB | 2397768 | 8/2004 |
| WO | 2007053022 | 5/2007 |
| WO | WO-2012080782 A1 * | 6/2012 | ......... A61L 24/0036 |

OTHER PUBLICATIONS

International Search Report dated Feb. 1, 2016 for PCT/IB2015/058416 (3 pages).

*Primary Examiner* — David H Willse
*Assistant Examiner* — Javier G Blanco
(74) *Attorney, Agent, or Firm* — Tutunjian & Bitetto, P.C.

(57) ABSTRACT

Disposable temporary spacer device for an articulation of the human body or for a bone cavity, wherein the spacer device includes at least one first component adapted to be constrained to a bone portion or end, wherein the spacer device is made from a biologically compatible material and comprises interconnected pores distributed in the entire volume occupied by the spacer device, in which the interconnected pores have a size and occupy a percentage of the volume of the spacer device such that it is able to absorb and consequently elute one or more pharmaceutical or medical substances in liquid or fluid form or in paste, cream, gel, wax, or viscous form.

4 Claims, 2 Drawing Sheets

(52) U.S. Cl.
CPC ............ *A61F 2002/30672* (2013.01); *A61F 2002/30677* (2013.01); *A61F 2310/0097* (2013.01); *A61L 2400/08* (2013.01)

(56) References Cited

U.S. PATENT DOCUMENTS

2010/0042214 A1* 2/2010 Nebosky ................ A61B 17/56
 623/16.11
2011/0208189 A1 8/2011 Faccioli et al.

* cited by examiner

ABSORBING ELUTING SPACER DEVICE

TECHNICAL FIELD OF THE INVENTION

The present invention concerns a disposable temporary spacer device for a joint of the human body or for a bone cavity, in particular a porous spacer device capable of absorbing and consequently eluting at least one pharmaceutical or medical substance.

Moreover, the present invention comprises a method for making a disposable temporary spacer device for a joint of the human body or for a bone cavity.

STATE OF THE ART

It is known that joint prostheses implanted at the joints of the human body can suffer infections.

When there is an infection, the implanted prosthesis must be removed and, before the implantation of a new prosthesis, it is necessary for the infection itself to be cured.

During such a period, spacer devices are often used, which are capable of maintaining the joint space, in order to eliminate the risk of atrophy or shortening of the muscles and of the tendons involved in a certain area.

Such procedure is known as "two-step treatment" for the removal and the implantation of a joint prosthesis.

Spacer devices usually used are porous since they are able, in contact with biological liquids, to elute the pharmaceutical or medical substances contained in them.

The elution of such substances is prolonged in time and, thanks to a targeted treatment, allows the infection in progress to be eliminated.

Such spacer devices, however, are usually already loaded for example with an antibiotic or with a medical substance and therefore it is not possible, for the surgeon, to select what type of substance to use.

There are also so-called static spacer devices, or bone fillers, which are implanted in a bone cavity of the human body in order to maintain a space suitable for the anatomical requirements of the patient or of the surgical implantation site.

However, known preformed spacers already contain an antibiotic substance, typically Gentamicin Sulfate.

However, surgeons would prefer to be able to adapt the pharmaceutical substance present in the spacers, or specifically the antibiotic contained in them, to the real and specific needs of the patient.

Therefore, sometimes surgeons prefer to use moulds in the operating room, with the drawback of having to mould the spacers, but with the advantage of deciding at that moment which pharmaceutical or antibiotic substances to insert in them, both in terms of the formulation or type and in terms of the quantities.

Therefore, there is a need to have a preformed spacer device that is able to absorb any type of substance, be it liquid or viscous, so as to meet the requirements of the surgeon and deal with the anatomical and pathological requirements of the patient.

In this way, it is possible to combine the advantages of having a preformed spacer device and at the same time of being able to select the pharmaceutical or medical substance to be inserted inside it.

BRIEF DESCRIPTION OF THE DRAWINGS

Further characteristics and advantages of the present invention will become clearer from the detailed description of a preferred, but not exclusive embodiment of a spacer device, illustrated for indicating but not limiting purposes in the attached tables of drawings, in which.

SUMMARY OF THE INVENTION

Figure 1:
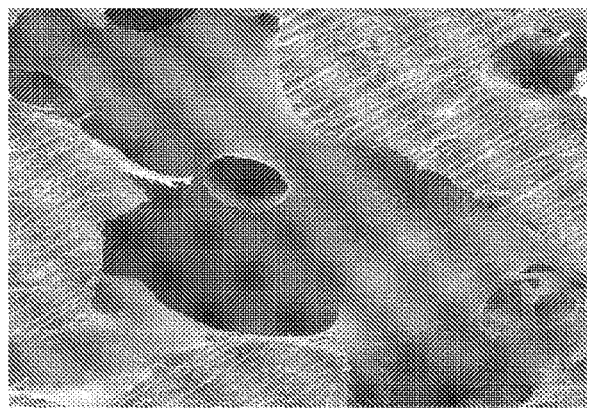
FIGS. 1 and 2 are scanning electron microscope (SEM) images of the spacer device according to the present invention, in which it is possible to see interconnected pores of large size.
Figure 2:
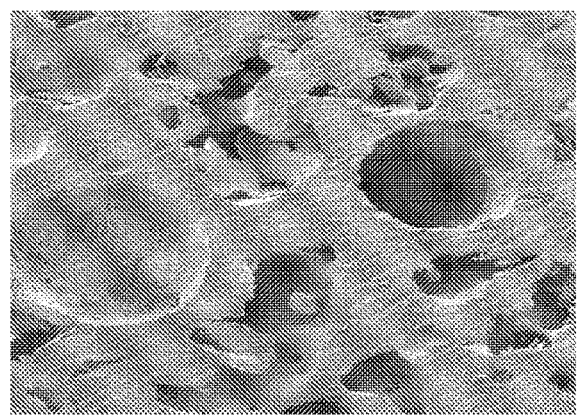

A purpose of the present invention is to improve the state of the art.

Another purpose of the present invention is to provide a spacer device that can be selected by the surgeon in terms of the material of which it consists, size of the porosity present in it and percentage of the porosity present in it.

Another purpose of the present invention is to provide a spacer device that is able to absorb and consequently elute one or more pharmaceutical or medical substances both in liquid or fluid form and in cream, gel or wax form, therefore more or less viscous substances.

In accordance with an aspect of the invention a spacer device is foreseen according to the present specification.

A further purpose of the present invention is to provide a method for making a spacer device that is versatile and quick.

In accordance with an aspect of the invention a method for making a spacer device according to the present specification is foreseen.

The present application refers to preferred and advantageous embodiments of the invention.

DETAILED DESCRIPTION OF THE INVENTION

The present invention concerns a disposable temporary spacer device for joints of the human body or for bone cavities. In particular, the spacer device according to the present invention can be articular or so-called static or a bone filler.

Such a spacer device is temporary in the sense that, once its healing function and that of maintaining the joint or bone space are carried out, it will be removed from the anatomical area in question and replaced for example with a permanent prosthesis. For this reason, it is preferred to avoid facilitating bone regrowth inside the spacer itself.

In particular, the spacer device according to the present invention is used for the treatment of infections that occur, for example, at the joints of the human body.

Moreover, the spacer device according to the present invention is able to maintain the joint space necessary in the joint or in the bone cavity of the human body, during the healing period of the infection, for example between the removal of an infected prosthesis and the implantation of a new joint prosthesis.

Such a spacer device makes it possible, for the time required for the treatment for example of the joint, to maintain the space necessary for the implantation of a new joint prosthesis and to ensure a good movement of the joint itself.

The spacer device according to a version of the present invention can be adapted to be implanted at the knee joint, hip joint, shoulder joint, elbow joint or any other joint present in the human body that can benefit from the use of a spacer device according to the present invention.

The spacer device, according to such a version of the invention, has a configuration substantially corresponding to the configuration of the joint that it will replace.

In this way, the spacer device according to the invention ensures good mobility of the joint and, therefore, a good quality of life for the patient waiting for the implantation of a new joint prosthesis.

In a further version, the spacer device according to the present invention has the function of a bone filler or so-called static spacer device, in other words not directly engaged by a joint of the human body nor involved in the support of loads.

Furthermore, the spacer device according to the present invention is compatible with the different sizes of the bone ends or cavities to which it is applied.

The spacer device according to the present invention comprises, at the generic and example level, but not limiting to the present invention, at least one first component, adapted to be constrained to a first bone end of a joint of a patient or to a bone cavity. The spacer device, according to a version of the invention, can also comprise a second component, adapted to be constrained for example to a second bone end of the joint of a patient.

For example, if the spacer device is applicable to the knee joint, it can comprise a first tibial component and a second femoral component.

In this case, the tibial component has a substantially plate-shaped configuration, on which the femoral component thereof articulates in a rotary or roto-translating manner If, on the other hand, the spacer device is suitable for being used at the hip joint, it can comprise a first component that substantially mimics the configuration of the head of the femur. Possible, there can be a hip socket or acetabulum component, in which the portion of the spacer device corresponding to the head of the femur is articulated.

Similarly, if it is a shoulder spacer device, there is a first component adapted to mimic in a substantially corresponding manner the head of the humerus, and possibly a second component, adapted to replace the glenoid cavity in the joint with the head of the humerus.

The spacer device according to the present invention, however, in a version of the invention, has a configuration that does not reproduce an entire portion of a joint, but only a part thereof.

The spacer device according to the present invention is preformed. The fact that it is preformed means that it is made by the manufacturer and has a substantially smooth outer surface without defects or machining burrs.

Moreover, the spacer device according to the present invention is made from a biologically compatible material.

Such a biologically compatible material is porous and has interconnected pores evenly distributed in the entire volume thereof.

Such biologically compatible material can be selected among plastic materials, such as polymethyl methacrylate (PMMA), polyvinyl chloride (PVC), polystyrene (PS), etc., ceramics, metals, metal alloys, organo-metallic compounds, and/or a combination thereof.

Specifically, the aforementioned plastic materials can be selected among thermoplastic polymers, such as acrylic resins, polyethylene, polypropylene, polyester, etc., thermoformable polymers, and other similar materials.

In a version of the present invention, the biologically compatible material is a bone cement based on polymethyl methacrylate (PMMA).

In a version of the invention, the aforementioned biologically compatible material is initially without pharmaceutical or medical substances. In a second version, the aforementioned biologically compatible material initially comprises at least one pharmaceutical or medical substance.

In any case, the main characteristic of a version of the spacer device according to the present invention is that of being equipped with a solid structure that is mechanically adequate to perform its spacer function, for example at the joint of the human body in which it must be implanted and, at the same time, of consisting of an absorbent biologically compatible material. Such an absorbent biologically compatible material is also eluent.

By eluent absorbent biologically compatible material we mean a material capable of absorbing one or more liquid or fluid solutions, hydrophilic or lipophilic, formed from a solvent and at least one pharmaceutical or medical substance (like for example an antibiotic substance, antitumor substance, anti-inflammatory substance, etc.) and of eluting them, once implanted and in contact with the tissues and the biological fluids, according to predetermined or desired temporal and speed kinetics.

In order to perform the aforementioned functions, the spacer device according to the present invention, as stated, is porous and has interconnected pores.

Such interconnected pores can, in a version, have a size on average smaller than 100 microns. In this case, the spacer device will be able to best perform the capillary absorption and consequent/successive elution function of solutions of pharmaceutical or medical substances, having a viscosity of less than 1000 cP (centipoise), like for example aqueous solutions of at least one antibiotic.

Such aqueous solutions are for example injectable solutions. However, in a further version, the interconnected pores can have average size comprised between 500 and 2000 micron or between 700 and 2000 micron, or even between 900 and 2000 micron or between 1000 and 2000 micron or between 1000 and 1800 micron or between 1300 1800 micron or approximately 1500-1600 micron.

The concept forming the basis of such a version of the invention is that the greater the size of the pores, the greater the capacity to absorb suspensions with viscosity of over 1000 cP of the pharmaceutical or medical substances.

Such average size generally comprised between 500 and 2000 micron makes it possible to absorb pharmaceutical or medical substances in the form of a viscous liquid having a viscosity of over 1000 cP, in other words highly viscous, or a paste, a creamy or waxy substance or even a gel, like for example polyvinyl alcohol or carboxy-methylcellulose or polyvinylpyrrolidone, etc.

By average size of the pores we mean the average value of their diameter or of their minimum two-dimensional size or of the side of the base constituting the opening or gap of the pore or of the width of their cross section according to a plane perpendicular to the main or longitudinal or largest dimension of the pore itself.

Therefore, the spacer device according to the invention has a permanent structural matrix, consisting of the material with which it is made, and such a matrix is spaced apart by interconnected pores that can have different sizes, according to what has been indicated previously.

Therefore, thanks to the spacer device according to the present invention, the surgeon can, having a preformed device, and therefore ready for use in terms of the overall structure and the surface finish, determine what is the type of porosity present in it both in terms of size, and the percentage with respect to the total volume occupied by the spacer device itself.

In particular, if the spacer device has small pores, of size smaller than 100 micron, it can by capillary action absorb a certain type of liquids or of fluids with low viscosity (below 1000 cP). In this way, the elution speed of such substances will be linked to the holding force of such pores and to the solubility of the liquids or low-viscosity fluids in contact with the biological fluids.

If, on the other hand, the spacer device has pores of larger size, for example generally comprised between 500 and 2000 micron, it can also absorb much more viscous liquids or substances, like for example the aforementioned substances in gel, cream, wax or similar In this case, as well as the holding force of such pores, the elution speed will also depend on the specific nature of such a substance and on their greater or lesser solubility in contact with the biological fluids.

In a version of the invention, in the presence of small pores the elution speed will be slow by virtue of the high liquid-capillary adhesion forces whereas in the presence of larger pores, the dilution speed will be fast by virtue of the lesser adhesion forces. However, the very viscous nature of the fluid in which the drug or the pharmaceutical or medical substance are dispersed, for example a biological wax, will make the elution of the medicament or of the pharmaceutical or medical substance slow or very slow.

In parallel, when the percentage of pores with respect to the total volume of the spacer is small, in other words approximately comprised between 4% and 30%, the amount of substance absorbed will be low, reducing the duration of the elution thereof.

In a version of the invention, the percentage in volume of interconnected pores over the total volume of the spacer device, is comprised between 4% and 70%.

On the other hand, in the presence of a spacer device or bone filler or static spacer device that is very porous, in which the percentage porosity with respect to the total volume of the spacer is high, in other words approximately comprised between 70% and 96%, the amount of substance absorbed is greater, and therefore the overall duration of the elution will also be longer.

Figure 3:
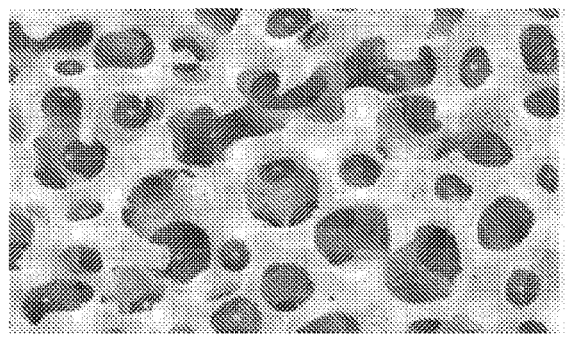
FIG. 3 is a scanning electron microscope (SEM) image of the spacer device according to the present invention, in which it is possible to see interconnected pores for a percentage greater than 70%.
Figure 4:
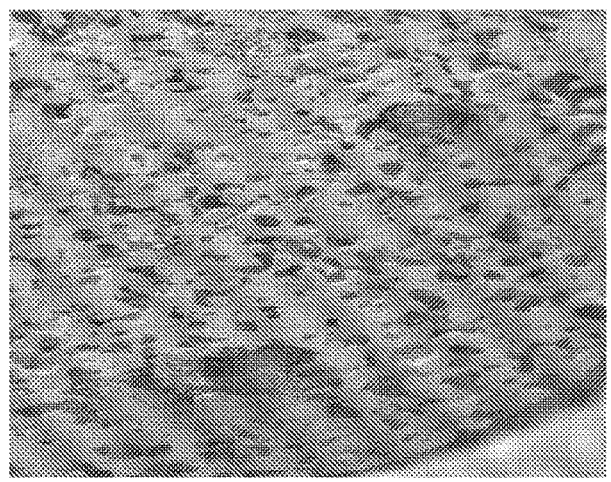
FIG. 4 is a scanning electron microscope (SEM) image of the spacer device according to the present invention, in which it is possible to see interconnected pores of a size smaller than 100 microns.

This type of spacer, as a consequence of the high porosity (as can be seen in FIG. 3), will have mechanical performance from low to very low, and therefore it will not be an articular spacer but rather a static spacer or a volumetric filler not loaded nor able to be loaded mechanically. A porosity of 96% is indeed that of a soft sponge.

Therefore, it can be seen how the possibilities for the surgeon to select the therapy to adopt and intervene on it, both in terms of the type of substance to be used, and in terms of the speed and duration of the treatment, are very wide and varied.

In this way, the surgeon, even with a preformed spacer device, can adapt it and the relative treatment to the specific needs to of patient.

Therefore, both in the version in which the spacer device initially lacks pharmaceutical or medical substances, and possibly in the version in which the spacer device is already loaded with at least one pharmaceutical or medical substance, based on the specific requirements of the surgeon based on the needs of the patient, thanks to the size and the percentage of the interconnected pores present in it, it will be possible to absorb or insert into it at least one (or a further) pharmaceutical or medical substance, or impregnate or even add to such a spacer device with it.

In a version of the invention, the spacer device according to the present invention can comprise a metallic core, in order to ensure, when needed, the necessary resistance to loads and therefore the necessary mechanical properties suitable for the implantation site.

Moreover, the duration and the amount of elution of the pharmaceutical or medical substance, whilst being able to be selected by the surgeon, are still suitable for effectively carrying out the required therapy and for the time necessary, for example, to cure the infection.

Based on the material from which the spacer device according to the present invention is made, the porosity, having the characteristics described above, can be obtained in various ways.

For example, the porosity in plastic materials can be produced by inserting, during the forming and moulding operations of the spacer device, in addition to the plastic material, usually in powder or pellet state, some additives like for example water, organic solvents, gases, or like colouring agents, or salts (non-toxic), or radiopaque agents, such as Barium sulfate, Zirconium oxide, bismuth oxide, ceramic powders or granules, polymers, fibres, substances with auxiliary function and useful for the specific surgical use, etc.

Of course, the size and the amount of additives, particularly of water, will correspond to the size and percentage porosity desired in the spacer, bone filler or static spacer device in question.

Such additives remain unbound to the plastic material.

If the spacer device is formed, for example, by means of heat, the powdered plastic material is added with water. The whole thing is arranged in an injection press that takes care of melting the plastic material that is then extruded in a mould. The water is not bonded by the molten plastic material but still remains dispersed in it. The cooled moulded manufactured product will be a solid of definite shape—corresponding to the spacer device in question—and equipped with high porosity due to the water that by evaporating leaves adjacent and intercommunicating or interconnected cavities.

If, on the other hand, the forming of the spacer device takes place by means of glue, the powdered plastic material, such as PMMA, PVC, PS, etc., is added with water and with a gluing means, like for example the solvent MMA, chloroform $CHCl_3$, Cyclohexanone, etc. The whole thing is placed in a mould. The water is not bonded by the plastic material, which has the single particles glued together, but still remains distributed in it. When the gluing means has completed its action, the mould is opened and the manufactured product is extracted, which will be a solid of definite shape—corresponding to the spacer device in question—and equipped with high porosity due to the water that by evaporating leaves adjacent and intercommunicating or interconnected cavities.

By means of the same processes, instead of the water or in addition to it, other additives can be used, obtaining a similar result.

If, on the other hand, the spacer device is made from ceramic, the porosity, whether or not the process foresees firing, it is obtained by adding the ceramic powder (for example feldspar, kaolin, etc.) with additives (for example water, organic solvents, gases, salts, sugars, etc.) which always remain unbonded to the ceramic. The malleable paste thus obtained is inserted in a mould and, after the various steps of consolidation of the mixture, the solidified manufactured product is extracted—corresponding to the spacer device in question.

Also in this case the additives previously inserted, being eliminated from the spacer device for example by evaporation or by solubilisation or by discharge, leave interconnected empty spaces that give the manufactured product and therefore the spacer device the desired porosity.

Finally, if the spacer device is made from a metallic material, the porosity can be obtained in various ways.

According to a first version, the mixture of metallic powders is arranged in a mould where it is compressed and heated. A partial welding of the powders is obtained at the points of contact granule-granule. Such a procedure can be known by the term sintering.

Between the various granules of metallic powder there remains an empty space with interconnected cavities—corresponding to the desired porosity—capable of developing capillary action and thus absorbing liquids.

According to a further version, the mixture of metallic powders is treated in a "laser sintering" machine. In this case, the granule-granule welding is carried out by a laser beam. In the same way, between the various granules of metallic powder there remains an empty space with interconnected cavities—corresponding to the desired porosity—capable of developing capillary action and thus absorbing liquids.

In these two cases, the additive can be considered air or a noble gas that remains comprised in the empty spaces present between granule and granule.

According to a further version, the mixture of metallic powders is added to with an organic powder (for example a polymer). The new mixture made up of metallic powders and polymer is taken into an injection press for plastic materials (for example with the MIM method). The polymer or the plastic material inserted in the new mixture, heated in the press, melts and gives to the whole the consistency of a fluid mass. Such a fluid mass is inserted or pushed into a mould from which solid moulded pieces (called "green") are obtained, which are arranged in a very high temperature furnace, in which the plastic component evaporates and the metal component is sintered. The product thus obtained—corresponding to the spacer device—is porous and capable of drawing or absorbing liquids or the desired pharmaceutical or medical substances.

Therefore, the method according to the present invention for making a spacer device comprises the step of providing a biologically compatible material, adding such a biologically compatible material with at least one additive comprising water, organic solvents, gases, salts, sugars, or colouring agents, or radiopaque agents such as barium sulfate, Zirconium oxide, bismuth oxide, ceramic powders or granules, polymers, fibres, substances with auxiliary function and useful for the specific surgical use, etc., forming or moulding the biologically compatible material in order to form the spacer device, eliminating the at least one additive from the spacer device in order to obtain interconnected pores distributed in the entire volume occupied by said spacer device, in which said interconnected pores have a size and occupy a percentage of the volume of the spacer device such that the spacer device is able to absorb and consequently elute one or more pharmaceutical or medical substances in liquid or fluid form or in paste, cream, gel, wax, or viscous form.

Such a method foresees that the step of forming or moulding comprises a step of moulding the biologically compatible material by means of heat or glue or in an injection press or by sintering or by means of laser sintering.

Moreover, the step of eliminating comprises evaporating, dissolving or solubilizing the at least one additive.

Finally, the method according to the present invention comprises, before the step of forming or moulding, a step of heating, melting or softening the biologically compatible material, and/or, after the step of forming or moulding, a step of cooling the spacer device.

The spacer device according to the present invention, being pre-formed, can have different overall dimensions, simplify the steps of implantation thereof into the seat of the joint or into the bone cavity or furthermore into the surgical site, without requiring further forming or modification operations in order to adapt its size to the implantation site.

In this way the time necessary to carry out the surgical intervention is indeed reduced.

The spacer device according to the present invention further comprises means for constraining to the bone ends or portions to which it is constrained. Such constraining means can be in the form of bone cement that is applied in fluid form and that then, by solidifying, firmly constrains the spacer device to the bone portion of interest. Alternatively, such constraining means can be screws or similar constraining elements, for example made from metallic material, which are fixed in suitable openings or seats if necessary foreseen in the spacer device itself.

Such constraining means in the form of screws or similar constraining elements can in turn then be fixed with fresh bone cement.

In this way, the patient can thus have a spacer device perfectly adapted to his actual bone and anatomical structure, in order to bear the loads required by the joint or by the bone cavity in question.

Moreover, the possibility of adding the spacer device with the appropriate pharmaceutical or medical products for the real needs, according to the specific decision of the surgeon, makes it possible to treat local infections in the site of the joint or in the bone cavity much more specifically or appropriately and to achieve the optimal conditions for the implantation of a new joint prosthesis.

Regarding this, as stated the spacer device performs the function of healing the bone infection by freeing the amount of antibiotic in the infected area. As far as such a function is concerned, the spacer manages to heal the infection by releasing antibiotic in a targeted manner, even in infinitesimal amounts, whereas the application of even high doses of antibiotic, but with methods that do not foresee the use of spacers, like for example washing of the infected location with high-dose antibiotic solutions, does not allow the same results to be obtained.

Studies carried out in the field have indeed shown that the bone tissue absorbs all of the (even few) molecules of antibiotic freed daily by the spacer in a concentrated manner This of course happens if the antibiotic is released by the spacer in contact with or next to the bone tissue, in which case the amount of antibiotic locally reaches the concentration that is effective in healing the infection. For this reason, it is essential for the spacer to extend for the entire area of the infection, by this meaning that if the infected prosthesis is a long prosthesis a long spacer will be used and in the case in which the infected prosthesis is of the short type a short spacer will be used. In the case in which a short spacer was placed where previously a long prosthesis was implanted, part of the bone would not be treated with antibiotic, in this way leaving bacteria free to proliferate.

Moreover, the spacer device according to the present invention, thanks to its specific features linked to the porosity present in it, can also be used as a drug delivery system, for example for anti-inflammatory substances, antitumor substances or antibiotics in general, in the site of interest.

The invention thus conceived can undergo numerous modifications and variants, all of which are covered by the inventive concept.

Moreover, all of the details can be replaced by other technically equivalent elements. In practice, the materials used, as well as the contingent shapes and sizes, can be whatever according to the requirements without for this reason departing from the scope of protection of the following claims.

In particular, characteristics described for one version of the invention can also be combined with other versions, without departing from the scope of protection of the following claims.

The invention claimed is:

1. A method for obtaining a disposable temporary removable spacer device for an articulation of the human body or for a bone cavity, the method comprising the following steps:
    arranging a nondegradable and nonresorbable biologically compatible material;
    adding, to such biologically compatible material, at least one additive;
    forming or molding said biologically compatible material together with said at least one additive for the purpose of forming said spacer device; and
    eliminating said at least one additive from said spacer device in order to obtain interconnected pores,
    wherein said eliminating step comprises evaporating, dissolving or solubilizing or discharging said at least one additive,
    wherein said interconnected pores consist of a size smaller than 100 microns and occupy a percentage of the volume of said spacer device such that said spacer device is able to absorb by capillary action, and consequently elute, one or more pharmaceutical or medical substances in liquid form to provide a healing function to said articulation or bone cavity,
    wherein said spacer device is preformed and said interconnected pores are uniformly distributed over the entire volume occupied by said spacer device,
    wherein the interconnected pores consisting of the size smaller than 100 microns prevent bone growth therein to enable removal of the spacer device from the articulation or bone cavity once its healing function and that of maintaining space of the articulation or bone cavity are carried out, and
    wherein said spacer device comprises at least one first component having bone-contacting surfaces adapted to be constrained to said articulation or bone cavity.

2. The method according to claim 1, wherein said step of forming or molding comprises a step of molding said biologically compatible material, by means of heat, adhesive or in an injection press, or by means of sintering or laser sintering.

3. The method according to claim 1, wherein said method, before said step of forming or molding, comprises heating, melting or softening said biologically compatible material and/or, after said step of forming or molding, comprises a step of cooling said spacer device.

4. The method according to claim 1, wherein the at least one additive comprises at least one of water, organic solvents, gas, salts, sugars, coloring agents, radiopaque agents, ceramic powders, ceramic granules, polymers and fibers.

* * * * *